United States Patent
Foster et al.

(10) Patent No.: US 10,174,371 B2
(45) Date of Patent: *Jan. 8, 2019

(54) USE OF TITANIUM NITRIDE AS AN ELECTRODE IN NON-FARADAIC ELECTROCHEMICAL CELL

(71) Applicant: Genia Technologies, Inc., Mountain View, CA (US)

(72) Inventors: John Foster, Mountain View, CA (US); Jason Komadina, Fremont, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/818,977

(22) Filed: Aug. 5, 2015

(65) Prior Publication Data
US 2017/0037467 A1 Feb. 9, 2017

(51) Int. Cl.
*C12Q 1/6874* (2018.01)
*C12Q 1/6869* (2018.01)
(Continued)

(52) U.S. Cl.
CPC ......... *C12Q 1/6874* (2013.01); *C12Q 1/6869* (2013.01); *C23C 14/0089* (2013.01); *C23C 14/0641* (2013.01); *C23C 14/345* (2013.01); *G01N 27/44791* (2013.01); *G01N 33/48721* (2013.01)

(58) Field of Classification Search
CPC .............. C12Q 1/6874; C12Q 1/6869; C23C 14/0089; C23C 14/0641; C23C 14/345; G01N 27/3278; G01N 27/44791; G01N 27/48721; H01L 29/401
See application file for complete search history.

(56) References Cited

U.S. PATENT DOCUMENTS

2008/0237674 A1* 10/2008 Ueda ............... H01L 21/823418
257/300
2011/0192723 A1* 8/2011 Chen ....................... B82Y 5/00
204/451

(Continued)

FOREIGN PATENT DOCUMENTS

JP 2013090576 5/2013

OTHER PUBLICATIONS

Y. Xie et al., Electrochemical capactiance performance of titanium nitride nanoarray, Materials Science and Engineering B 178, pp. 1443-1451 (2013).*

(Continued)

*Primary Examiner* — Maris R Kessel
(74) *Attorney, Agent, or Firm* — Van Pelt, Yi & James LLP

(57) ABSTRACT

A nanopore cell includes a conductive layer. The nanopore cell further includes a titanium nitride (TiN) working electrode disposed above the conductive layer. The nanopore cell further includes insulating walls disposed above the TiN working electrode, wherein the insulating walls and the TiN working electrode form a well into which an electrolyte may be contained. In some embodiments, the TiN working electrode comprises a spongy and porous TiN working electrode that is deposited by a deposition technique with conditions tuned to deposit sparsely-spaced TiN columnar structures or columns of TiN crystals above the conductive layer.

8 Claims, 18 Drawing Sheets

(51) Int. Cl.
*G01N 33/487* (2006.01)
*C23C 14/00* (2006.01)
*C23C 14/06* (2006.01)
*C23C 14/34* (2006.01)
*G01N 27/447* (2006.01)

(56) References Cited

U.S. PATENT DOCUMENTS

| | | |
|---|---|---|
| 2014/0034497 A1 | 2/2014 | Davis et al. |
| 2016/0216233 A1* | 7/2016 | Hovis .............. G01N 33/48721 |
| 2016/0258939 A1* | 9/2016 | Morin .............. G01N 33/54366 |
| 2017/0058397 A1* | 3/2017 | Mager ..................... C23C 14/35 |
| 2017/0059546 A1* | 3/2017 | Foster ............. G01N 33/48721 |

OTHER PUBLICATIONS

M. K. Patan, Titanium Nitride as an Electrode Material for High Charge Density Applications, NJIT, Dept. of Electr. and Comp. Eng., May 2007.*

Patsalas et al., The Effect of Substrate Temperature and Biasing on the Mechanical Properties and Structure of Sputtered Titanium Nitride Thin Films, Surface and Coatings Technology 125, 2000, pp. 335-340.

* cited by examiner

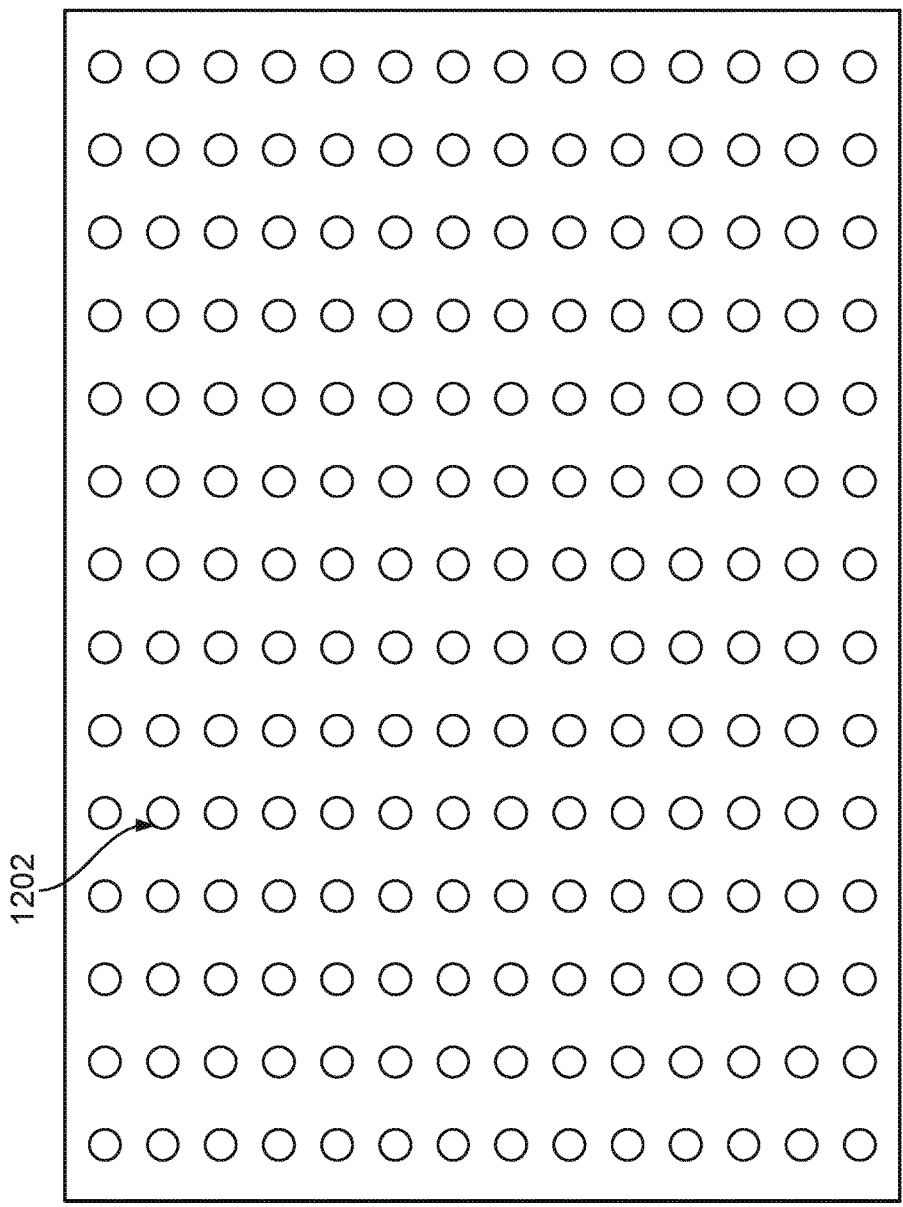

US 10,174,371 B2

USE OF TITANIUM NITRIDE AS AN ELECTRODE IN NON-FARADAIC ELECTROCHEMICAL CELL

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 12 illustrates a top view of a plurality of circular openings 1202 of a plurality of wells in a nanopore based sequencing chip.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
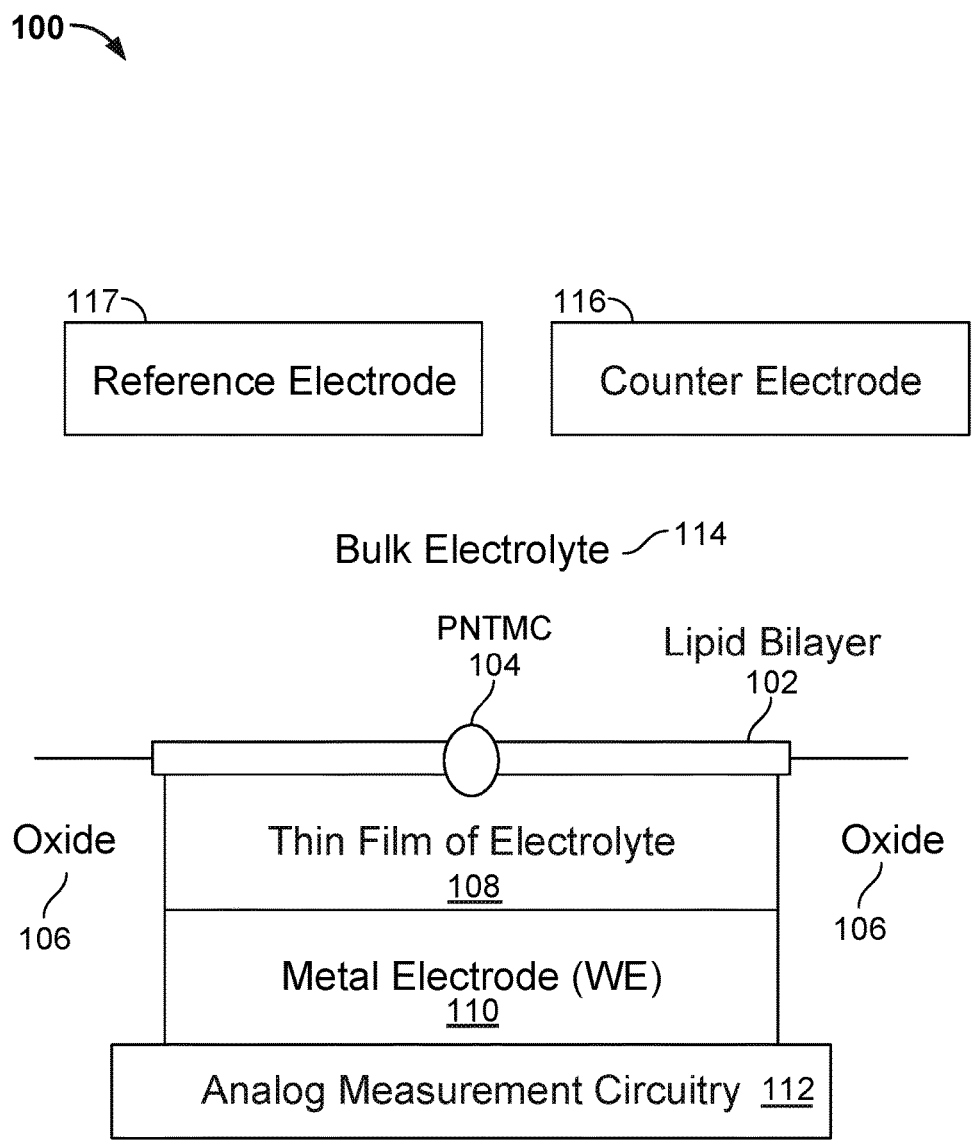
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to an electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116. The cell also includes a reference electrode 117, which acts as an electrochemical potential sensor.

Figure 2:
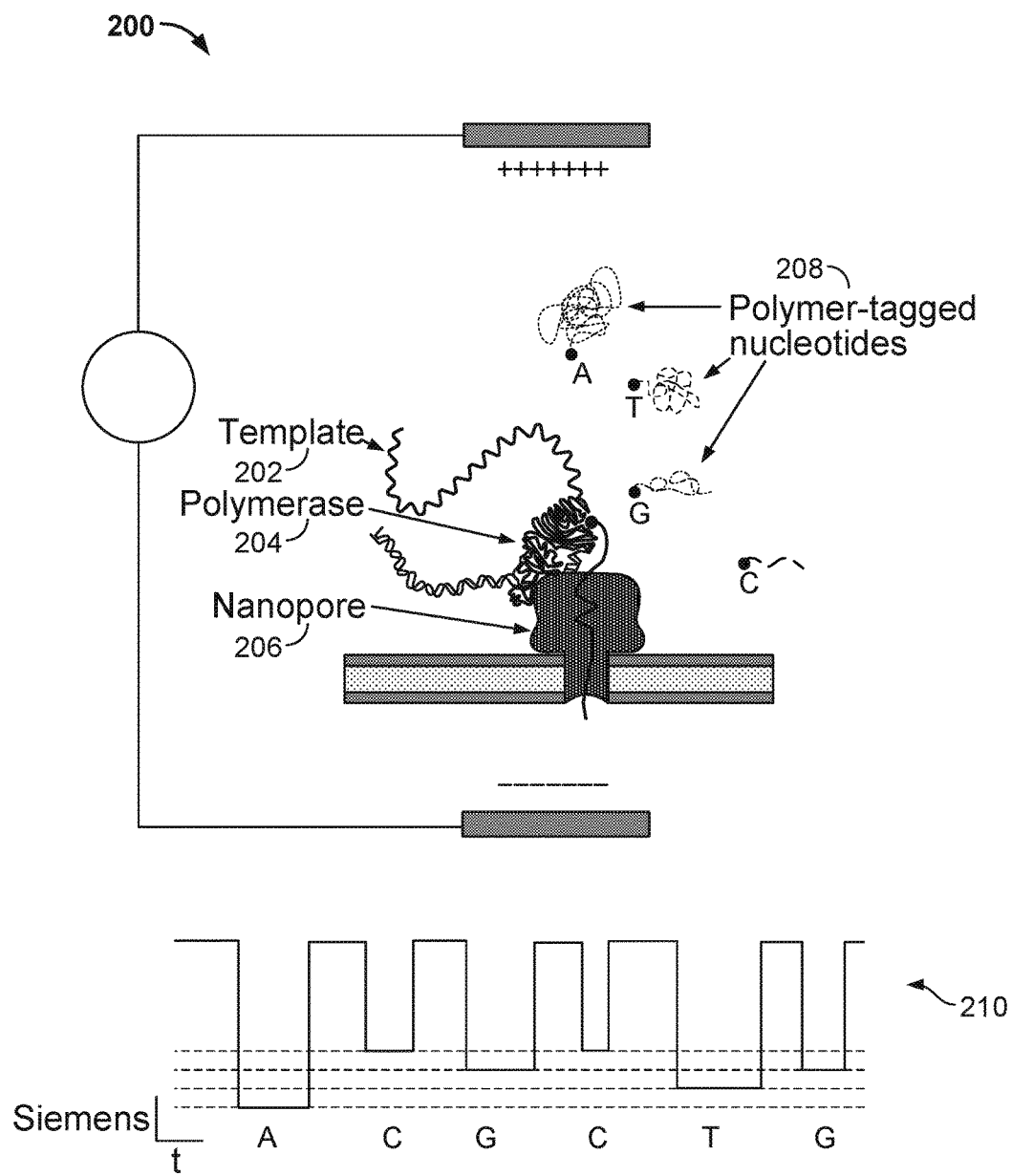
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
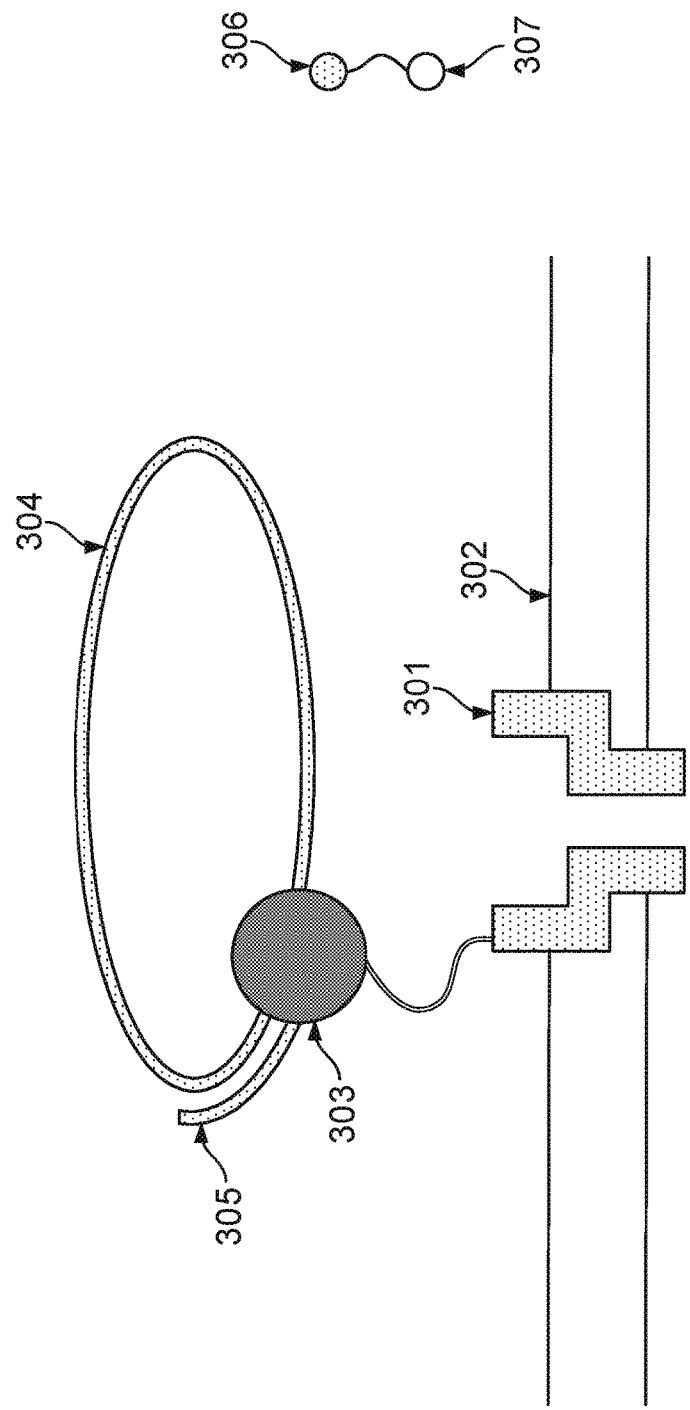
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
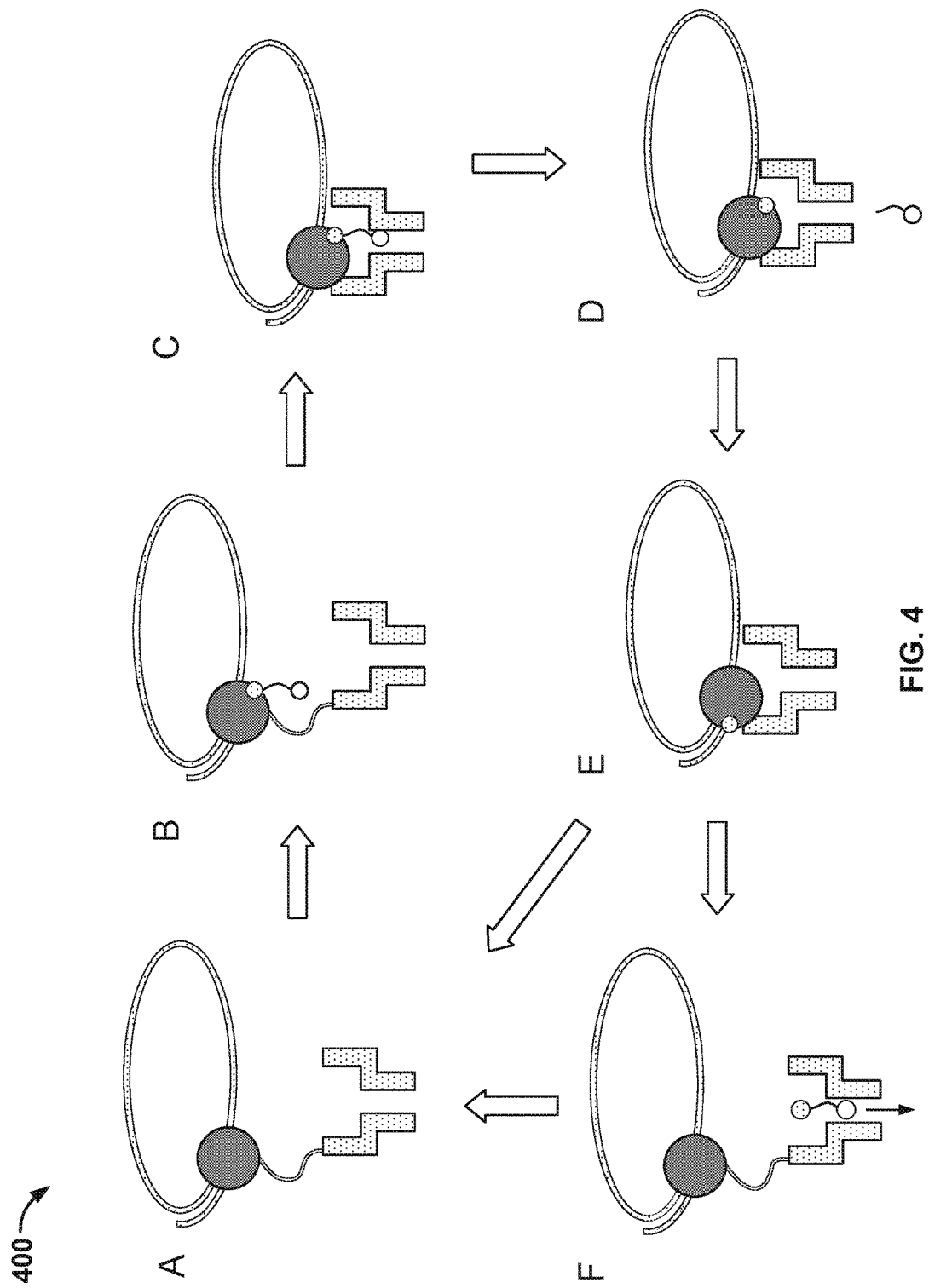
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
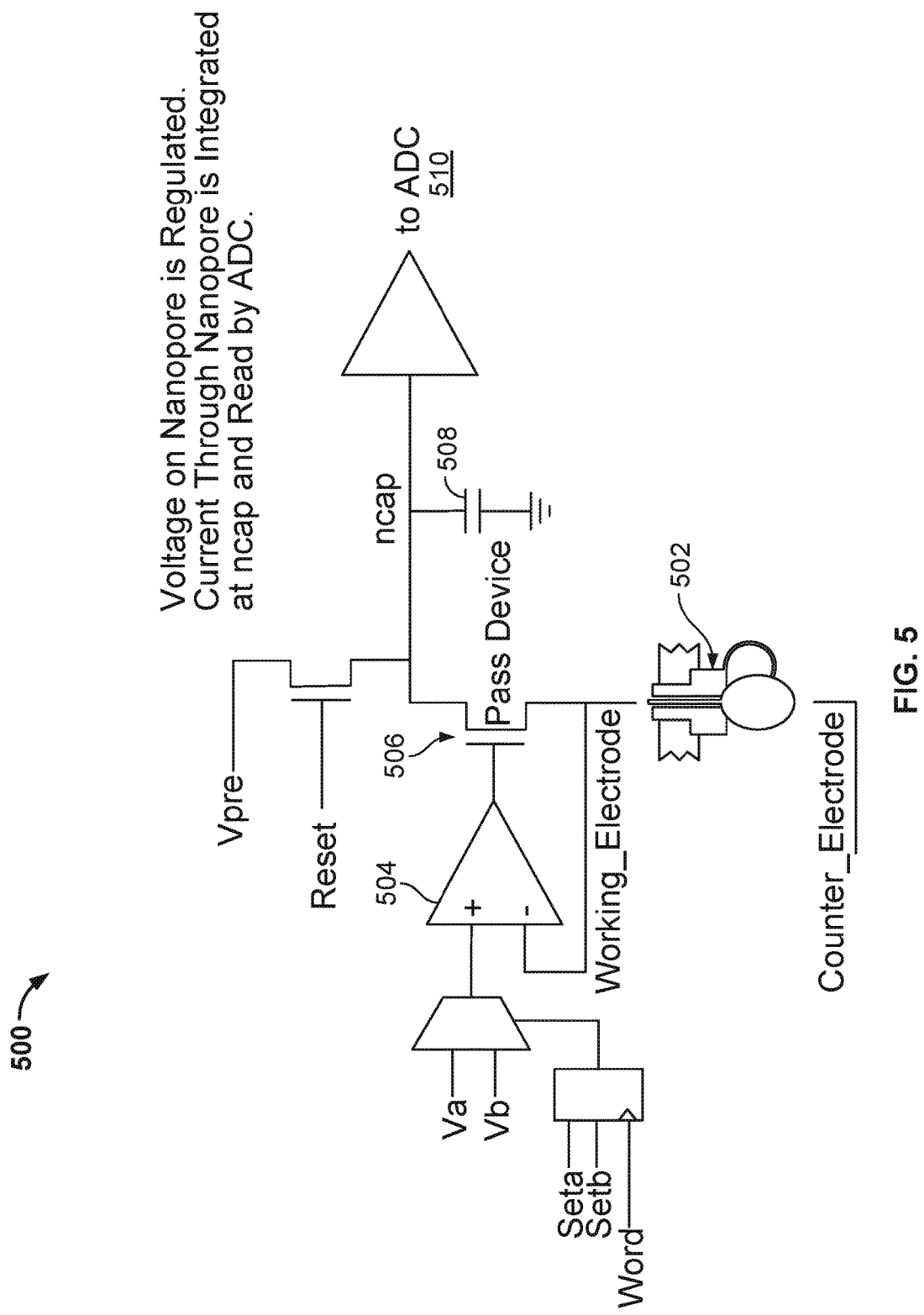
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues. For example, it may exacerbate the offset and noise problems in the cells even further.

Figure 6:
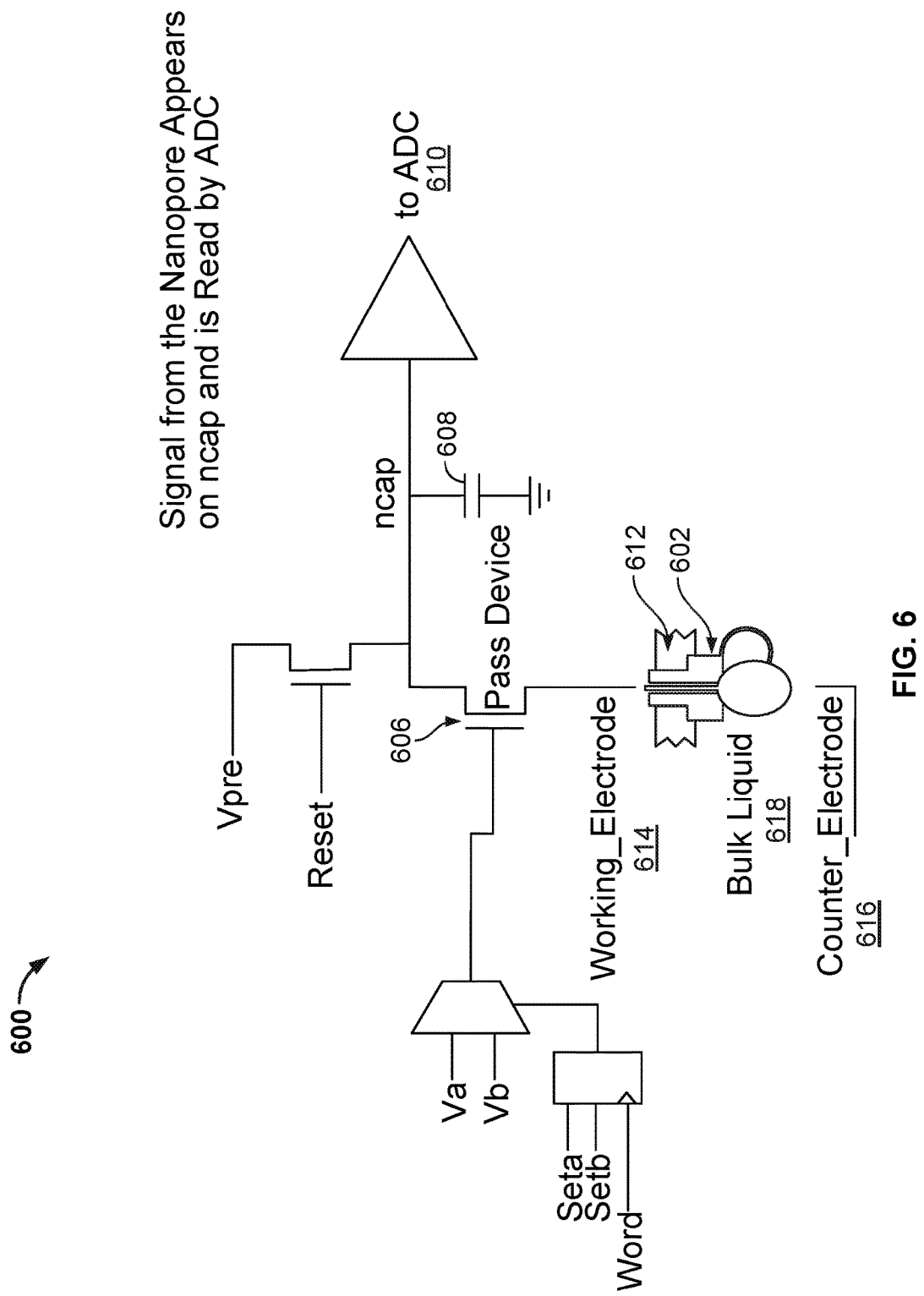
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
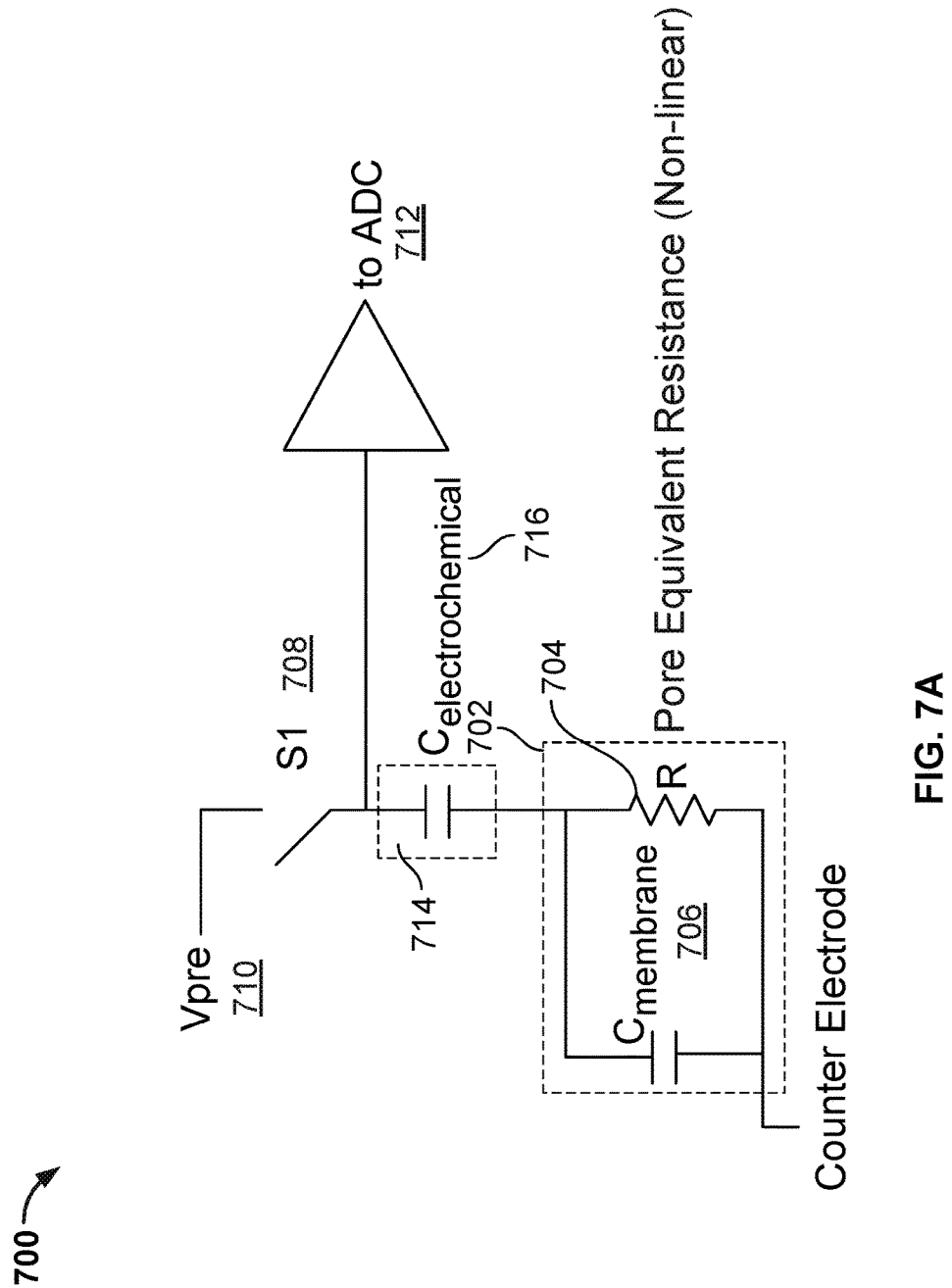
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
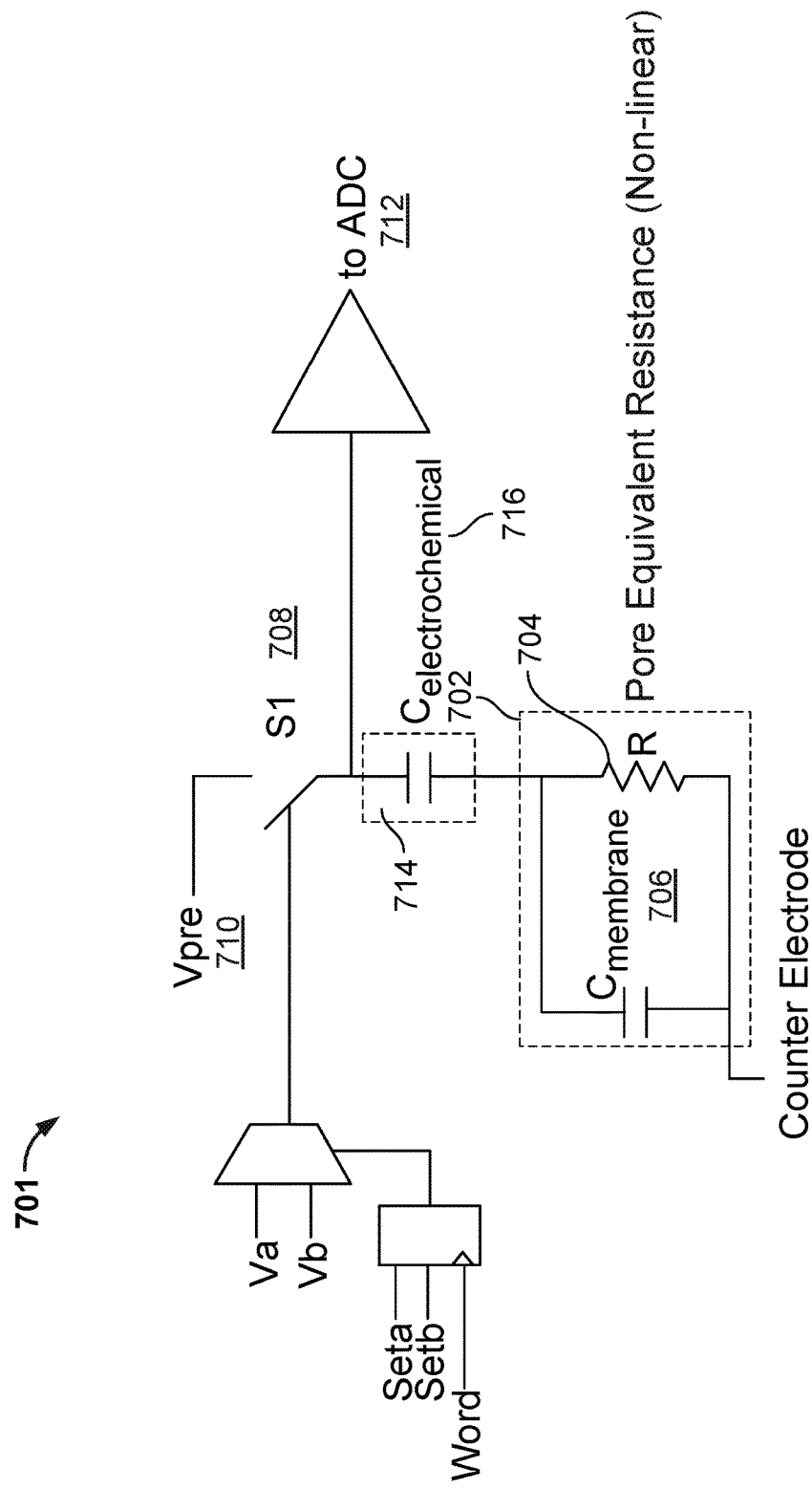
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane and an electrical model 714 representing the electrical properties of the working electrode are shown. Note in FIGS. 7A and 7B that the respective circuitry does not require an extra capacitor (e.g., $n_{cap}$ 508 in FIG. 5) to be fabricated on-chip, thereby facilitating the reduction in size of the nanopore based sequencing chip.

Electrical model 702 includes a capacitor 706 that models a capacitance associated with the membrane ($C_{membrane}$) and a resistor 704 that models a resistance associated with the nanopore in different states (e.g., the open-channel state or the states corresponding to having different types of tags or molecules inside the nanopore). Electrical model 714 includes a capacitor 716 that models a capacitance associated with the working electrode. The capacitance associated with the working electrode is also referred to as an electrochemical capacitance ($C_{electrochemical}$). The electrochemical capacitance $C_{electrochemical}$ associated with the working electrode includes a double-layer capacitance and may further include a pseudocapacitance.

Figure 7C:
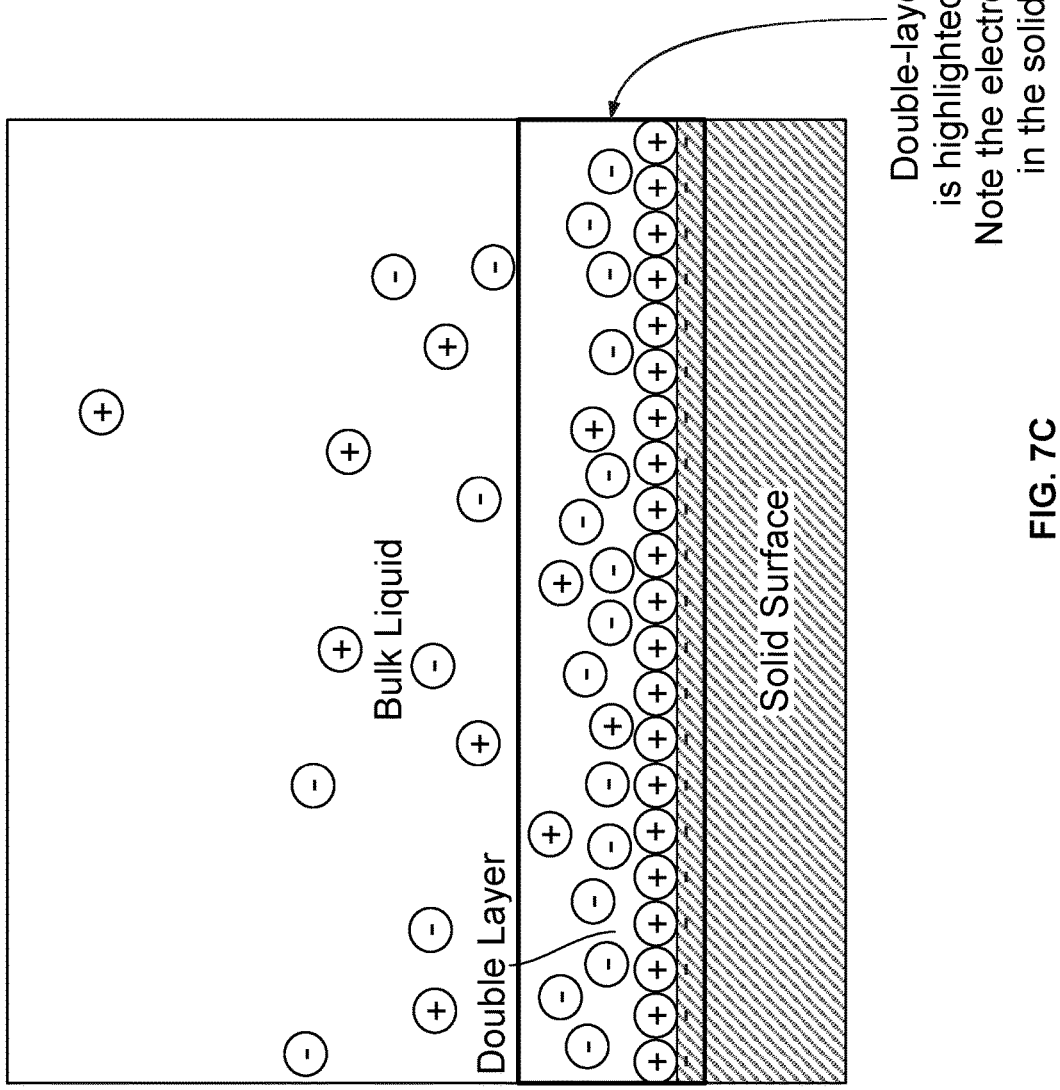
FIG. 7C illustrates a double layer that is formed at any interface between a conductive electrode and an adjacent liquid electrolyte. In the example shown, the electrode surface is negatively charged, resulting in the accumulation of positively charged species in the electrolyte. In another example, the polarity of all charges shown may be opposite to the example shown.

FIG. 7C illustrates a double layer that is formed at any interface between a conductive electrode and an adjacent liquid electrolyte. If a voltage is applied, electronic charges (positive or negative) accumulate in the electrode at the interface between the conductive electrode and adjacent liquid electrolyte. The charge in the electrode is balanced by reorientation of dipoles and accumulation of ions of opposite charge in the electrolyte near the interface. The accumulation of charges on either side of the interface between electrode and electrolyte, separated by a small distance due to the finite size of charged species and solvent molecules in the electrolyte, acts like a dielectric in a conventional capacitor. The term "double layer" refers to the ensemble of electronic and ionic charge distribution in the vicinity of the interface between the electrode and electrolyte.

Figure 7D:
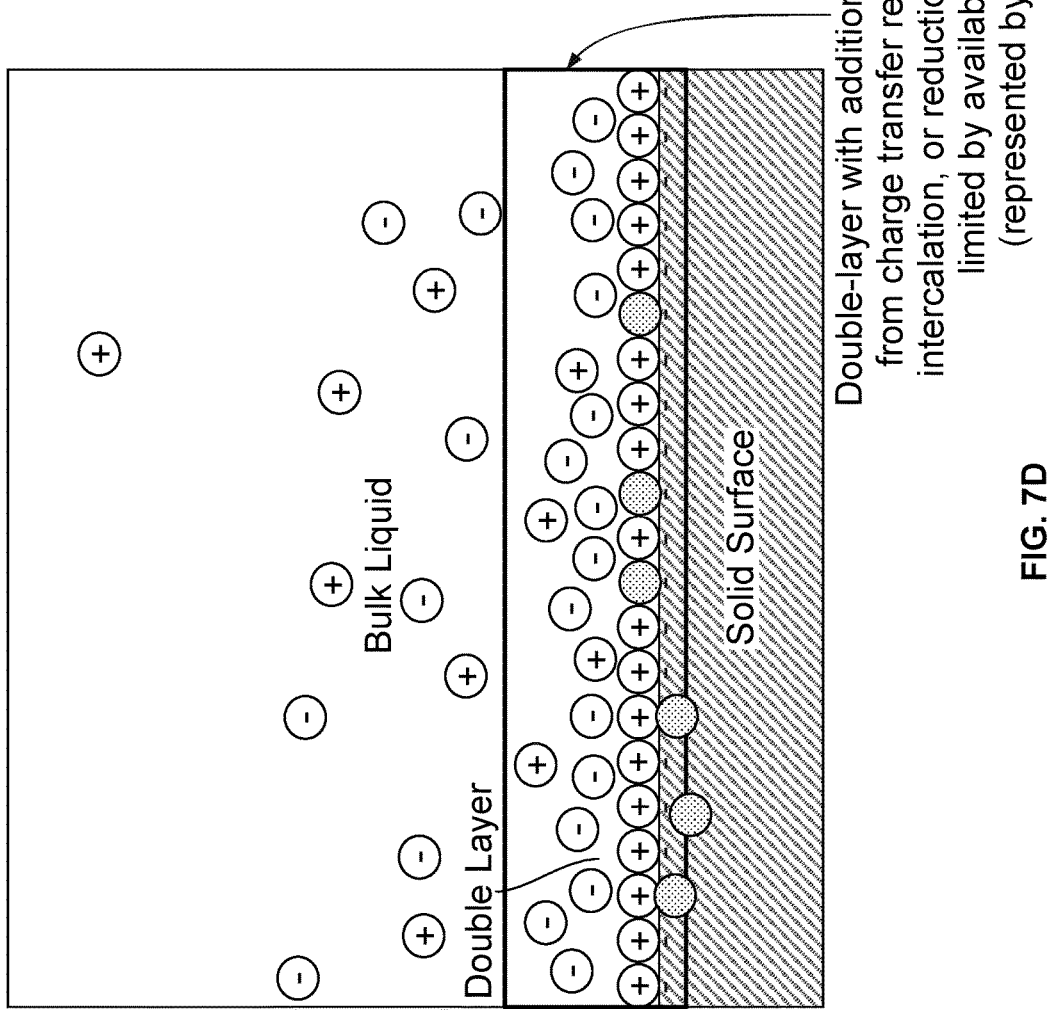
FIG. 7D illustrates a pseudocapacitance effect that can be formed, simultaneously with the formation of a double-layer as in FIG. 7C, at an interface between a conductive electrode and an adjacent liquid electrolyte.

FIG. 7D illustrates a pseudocapacitance effect that can be formed, simultaneously with the formation of a double-layer as in FIG. 7C, at an interface between a conductive electrode and an adjacent liquid electrolyte. A pseudocapacitor stores electrical energy faradaically by electron charge transfer between the electrode and the electrolyte. This is accomplished through electrosorption, reduction-oxidation reactions, or intercalation processes.

Figure 8:
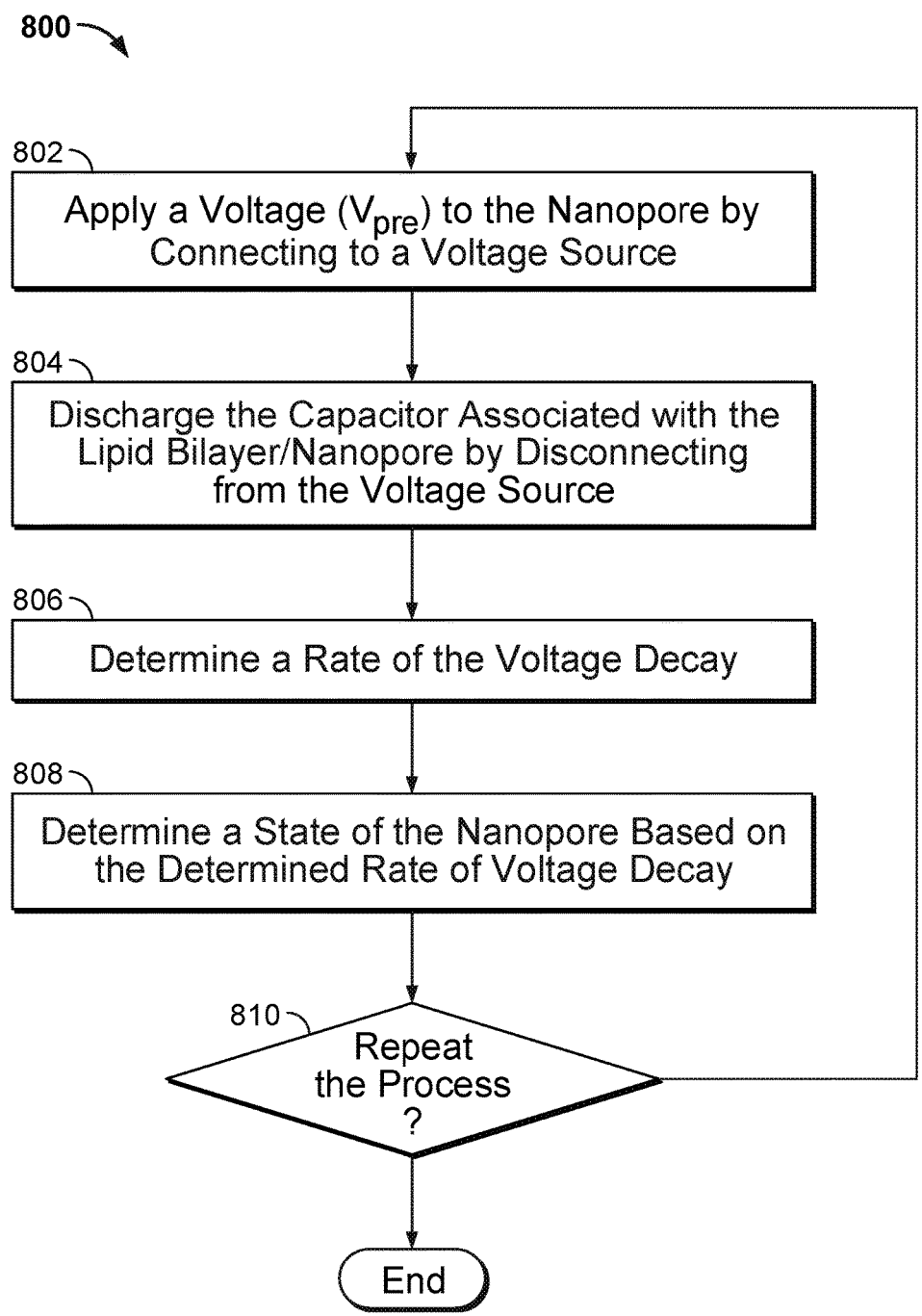
FIG. 8 illustrates an embodiment of a process 800 for analyzing a molecule inside a nanopore, wherein the nanopore is inserted in a membrane.
Figure 9:
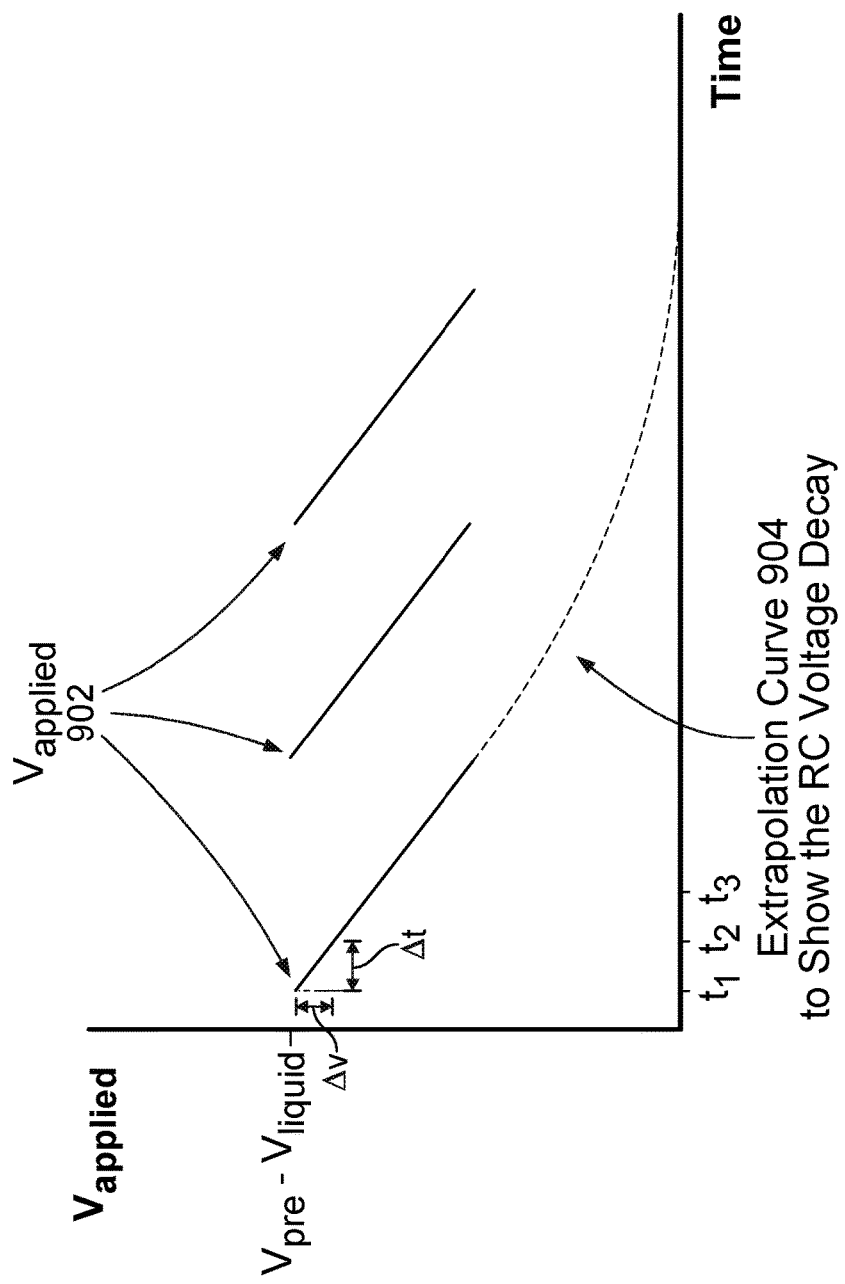
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. The voltage across the nanopore changes over time. The rate of the voltage decay (i.e., the steepness of the slope of the voltage across the nanopore versus time plot) depends on the cell resistance (e.g., the resistance of resistor 704 in FIG. 7A). More particularly, as the resistances associated with the nanopore in different states (e.g., the states corresponding to having different types of molecules inside the nanopore) are different due to the molecules' distinct chemical structure, different corresponding rates of voltage decay may be observed and thus may be used to identify the molecule in the nanopore.

Figure 10:
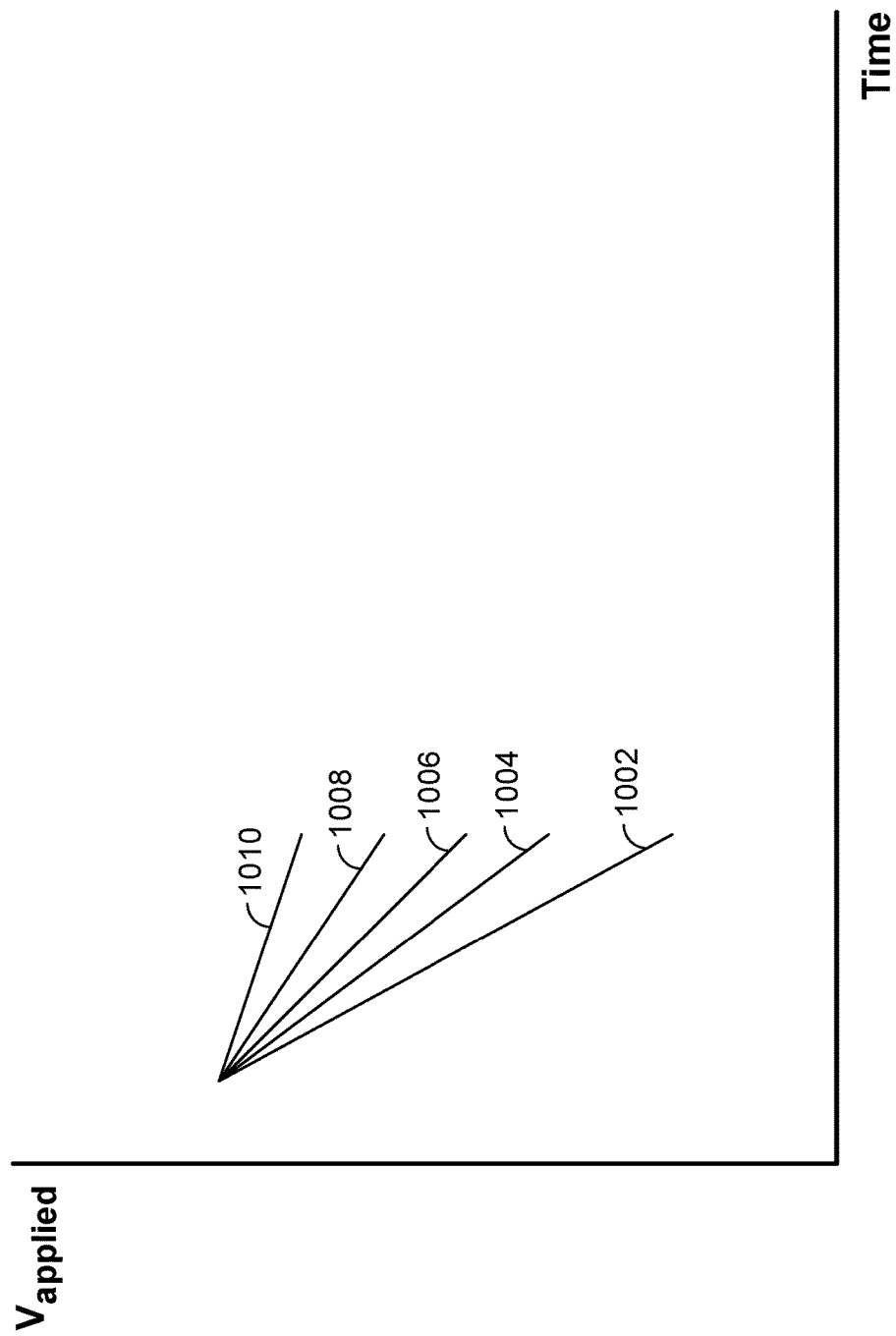
FIG. 10 illustrates an embodiment of the plots of the voltage applied across the nanopore versus time when the nanopore is in different states.

FIG. 10 illustrates the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

Allowing the voltage applied across the nanopore to decay over a time period during which the nanopore is in a particular detectable state has many advantages. One of the advantages is that the elimination of the operational amplifier, the pass device, and the capacitor (e.g., $n_{cap}$ 508 in FIG. 5) that are otherwise fabricated on-chip in the cell circuitry significantly reduces the footprint of a single cell in the nanopore based sequencing chip, thereby facilitating the scaling of the nanopore based sequencing chip to include more and more cells (e.g., incorporating millions of cells in a nanopore based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to create the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. For example, they can be used to correct for baseline drift arising from AC-non-faradaic operation.

Increased cell performance of the nanopore based sequencing chip may be achieved by maximizing the electrochemical capacitance (see $C_{electrochemical}$ 716 of FIGS. 7A and 7B) associated with the working electrode. By maximizing $C_{electrochemical}$, the information signal measured by the circuitries shown in FIG. 6, 7A, or 7B becomes more stable and the spurious signal convoluted on top of the information signal is minimized. $C_{electrochemical}$ is maximized such that the impedance associated with $C_{electrochemical}$ is close to an AC (alternating current) short circuit compared with the impedance associated with $C_{membrane}$ (see $C_{membrane}$ 706 of FIGS. 7A and 7B).

In the present application, a non-faradaic electrochemical cell for nucleic acid sequencing that includes a titanium nitride (TiN) working electrode with increased electrochemical capacitance is disclosed. As will be described in greater detail below, the TiN working electrode is grown and deposited in such a manner that a rough, spongy, and porous electrode with sparsely-spaced columnar structures of TiN is formed.

Figure 11:
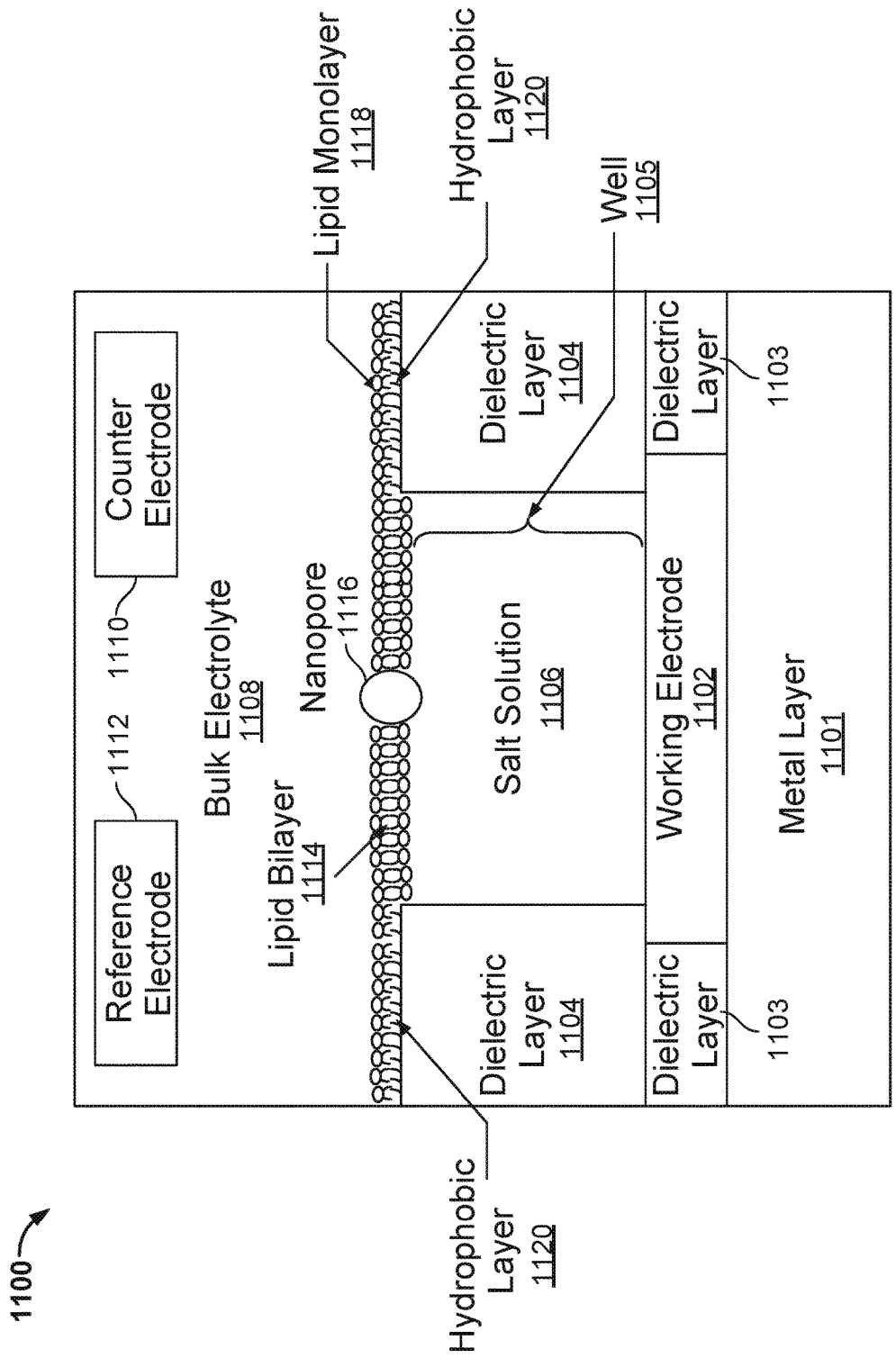
FIG. 11 illustrates an embodiment of a non-faradaic electrochemical cell 1100 of a nanopore based sequencing chip that includes a TiN working electrode with increased electrochemical capacitance.

FIG. 11 illustrates an embodiment of a non-faradaic electrochemical cell 1100 of a nanopore based sequencing chip that includes a TiN working electrode with increased electrochemical capacitance. Cell 1100 includes a conductive or metal layer 1101. Metal layer 1101 connects cell 1100 to the remaining portions of the nanopore based sequencing chip. In some embodiments, metal layer 1101 is the metal 6 layer (M6). Cell 1100 further includes a working electrode 1102 and a dielectric layer 1103 above metal layer 1101. In some embodiments, working electrode 1102 is circular or octagonal in shape and dielectric layer 1103 forms the walls surrounding working electrode 1102. Cell 1100 further includes a dielectric layer 1104 above working electrode 1102 and dielectric layer 1103. Dielectric layer 1104 forms the insulating walls surrounding a well 1105. In some embodiments, dielectric layer 1103 and dielectric layer 1104 together form a single piece of dielectric. Dielectric layer 1103 is the portion that is disposed horizontally adjacent to working electrode 1102, and dielectric layer 1104 is the portion that is disposed above and covering a portion of the working electrode. In some embodiments, dielectric layer 1103 and dielectric layer 1104 are separate pieces of dielectric and they may be grown separately. Well 1105 has an opening above an uncovered portion of the working electrode. In some embodiments, the opening above the uncovered portion of the working electrode is circular or octagonal in shape. FIG. 12 illustrates a top view of a plurality of circular openings 1202 of a plurality of wells in a nanopore based sequencing chip.

Inside well 1105, a film of salt solution/electrolyte 1106 is deposited above working electrode 1102. Salt solution 1106 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the film of salt solution 1106 has a thickness of about three microns (μm). The thickness of the film of salt solution 1106 may range from 0-5 microns.

Dielectric material used to form dielectric layers 1103 and 1104 includes glass, oxide, silicon mononitride (SiN), and the like. The top surface of dielectric layer 1104 may be silanized. Silanization forms a hydrophobic layer 1120 above the top surface of dielectric layer 1104. In some embodiments, hydrophobic layer 1120 has a thickness of about 1.5 nanometer (nm). Alternatively, dielectric material that is hydrophobic such as hafnium oxide may be used to form dielectric layer 1104.

As shown in FIG. 11, a membrane is formed on top of dielectric layer 1104 and spans across well 1105. For example, the membrane includes a lipid monolayer 1118 formed on top of hydrophobic layer 1120 and as the membrane reaches the opening of well 1105, the lipid monolayer transitions to a lipid bilayer 1114 that spans across the opening of the well. Hydrophobic layer 1120 facilitates the formation of lipid monolayer 1118 above dielectric layer 1104 and the transition from a lipid monolayer to a lipid bilayer. A bulk electrolyte 1108 containing protein nanopore transmembrane molecular complexes (PNTMC) and the analyte of interest is placed directly above the well. A single PNTMC/nanopore 1116 is inserted into lipid bilayer 1114 by electroporation. Nanopore 1116 crosses lipid bilayer 1114 and provides the only path for ionic flow from bulk electrolyte 1108 to working electrode 1102. Bulk electrolyte 1108 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Cell 1100 includes a counter electrode (CE) 1110. Cell 1100 also includes a reference electrode 1112, which acts as an electrochemical potential sensor. In some embodiments, counter electrode 1110 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

Working electrode 1102 is a titanium nitride (TiN) working electrode with increased electrochemical capacitance. The electrochemical capacitance associated with working electrode 1102 may be increased by maximizing the specific surface area of the electrode. The specific surface area of working electrode 1102 is the total surface area of the electrode per unit of mass (e.g., $m^2/kg$) or per unit of volume (e.g., $m^2/m^3$ or $m^{-1}$) or per unit of base area (e.g., $m^2/m^2$). As the surface area increases, the electrochemical capacitance of the working electrode increases, and a greater amount of ions can be displaced with the same applied potential before the capacitor becomes charged. The surface area of working electrode 1102 may be increased by making the TiN electrode "spongy" or porous. The TiN sponge soaks up electrolyte and creates a large effective surface area in contact with the electrolyte.

The ratio of the capacitance associated with the membrane (see $C_{membrane}$ 706 of FIGS. 7A and 7B) and the capacitance associated with the working electrode (see $C_{electrochemical}$ 716 of FIGS. 7A and 7B) may be adjusted to achieve optimal overall system performance. Increased system performance may be achieved by reducing $C_{membrane}$ while maximizing $C_{electrochemical}$. $C_{membrane}$ is adjusted to create the required RC time constant without the need for additional on-chip capacitance, thereby allowing a significant reduction in cell size and chip size.

In cell 1100, the base surface area of the opening of well 1105 (which is the same as the base surface area of lipid bilayer 1114) and the base surface area of working electrode 1102 are determined by the dimensions of dielectric layer 1104 and dielectric layer 1103, respectively. The base surface area of working electrode 1102 is greater than or equal to the base surface area of the opening of well 1105. Therefore, the two base surface areas may be optimized independently to provide the desired ratio between $C_{membrane}$ and $C_{electrochemical}$. As shown in FIG. 11, a portion of working electrode 1102 is covered by dielectric 1104 and therefore the covered portion does not have direct contact with salt solution/electrolyte 1106. By using a spongy and porous TiN working electrode, the electrolyte can diffuse through the spaces between the columnar TiN structures and vertically down the uncovered portion of the working electrode and then horizontally to the covered portion of working electrode 1102 that is underneath dielectric layer 1104. As a result, the effective surface area of TiN that is in contact with the electrolyte is maximized and $C_{electrochemical}$ is maximized.

FIGS. 13A-13E illustrate an embodiment of a process for constructing a non-faradaic electrochemical cell of a nanopore based sequencing chip that includes a TiN working electrode with increased electrochemical capacitance.

Figure 13A:
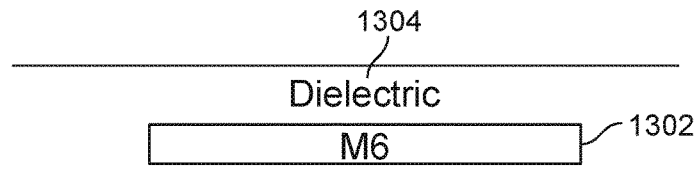
FIGS. 13A-13E illustrate an embodiment of a process for constructing a non-faradaic electrochemical cell of a nanopore based sequencing chip that includes a TiN working electrode with increased electrochemical capacitance.

FIG. 13A illustrates step A of the process. At step A, a layer of dielectric 1304 (e.g., SiO$_2$) is disposed on top of a conductive layer 1302 (e.g, M6). The conductive layer includes circuitries that deliver the signals from the cell to the rest of the chip. For example, the circuitries deliver signals from the cell to an integrating capacitor. In some embodiments, the layer of dielectric 1304 has a thickness of about 400 nm.

Figure 13B:
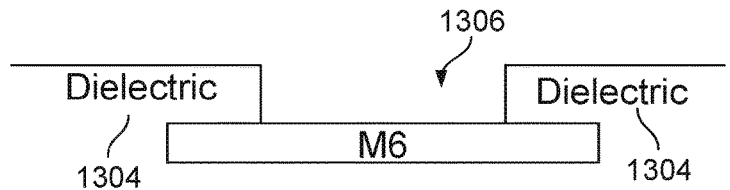

FIG. 13B illustrates step B of the process. At step B, the layer of dielectric 1304 is etched to create a hole 1306. The hole 1306 provides a space for growing the spongy and porous TiN electrode.

Figure 13C:
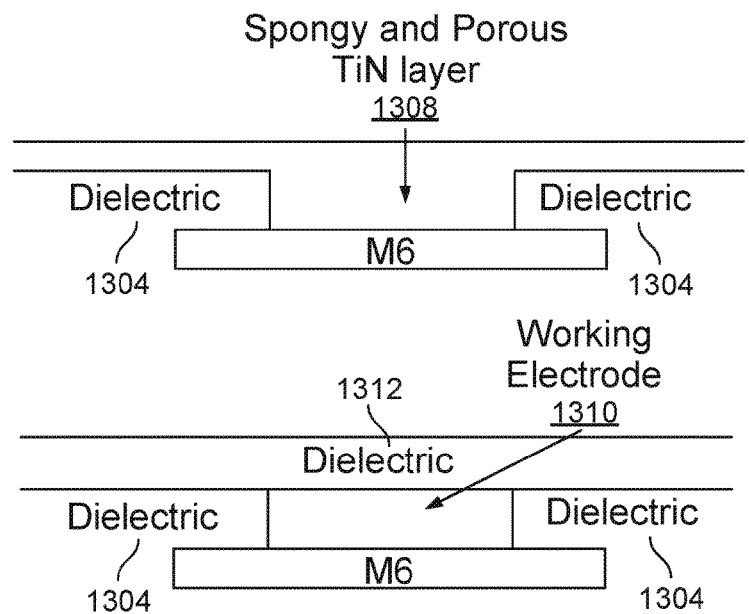

FIG. 13C illustrates step C of the process. At step C, a spongy and porous TiN layer 1308 is deposited to fill the hole 1306 created at step B. The spongy and porous TiN layer 1308 is grown and deposited in a manner to create rough, sparsely-spaced TiN columnar structures or columns of TiN crystals that provide a high specific surface area that can come in contact with an electrolyte. The layer of spongy and porous TiN layer 1308 can be deposited using different deposition techniques, including atomic layer deposition, chemical vapor deposition, physical vapor deposition (PVD) sputtering deposition, and the like. For example, layer 1308 may be deposited by chemical vapor deposition using TiCl$_4$ in combination with nitrogen containing precursors (e.g., NH$_3$ or N$_2$). Layer 1308 may also be deposited by chemical vapor deposition using TiCl$_4$ in combination with titanium and nitrogen containing precursors (e.g., tetrakis-(dimethylamido) titanium (TDMAT) or tetrakis-(diethylamido) titanium TDEAT). Layer 1308 may also be deposited by PVD sputtering deposition. For example, titanium can be reactively sputtered in an N$_2$ environment or directly sputtered from a TiN target. The conditions of each of the deposition methods may be tuned in such a way to deposit sparsely-spaced TiN columnar structures or columns of TiN crystals. For example, when layer 1308 is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals. In some embodiments, the depth of the deposited layer 1308 is about 1.5 times the depth of hole 1306. The depth of the deposited layer 1308 is between 500 angstroms to 3 microns thick. The diameter or width of the deposited layer 1308 is between 20 nm to 100 microns.

Figure 14:
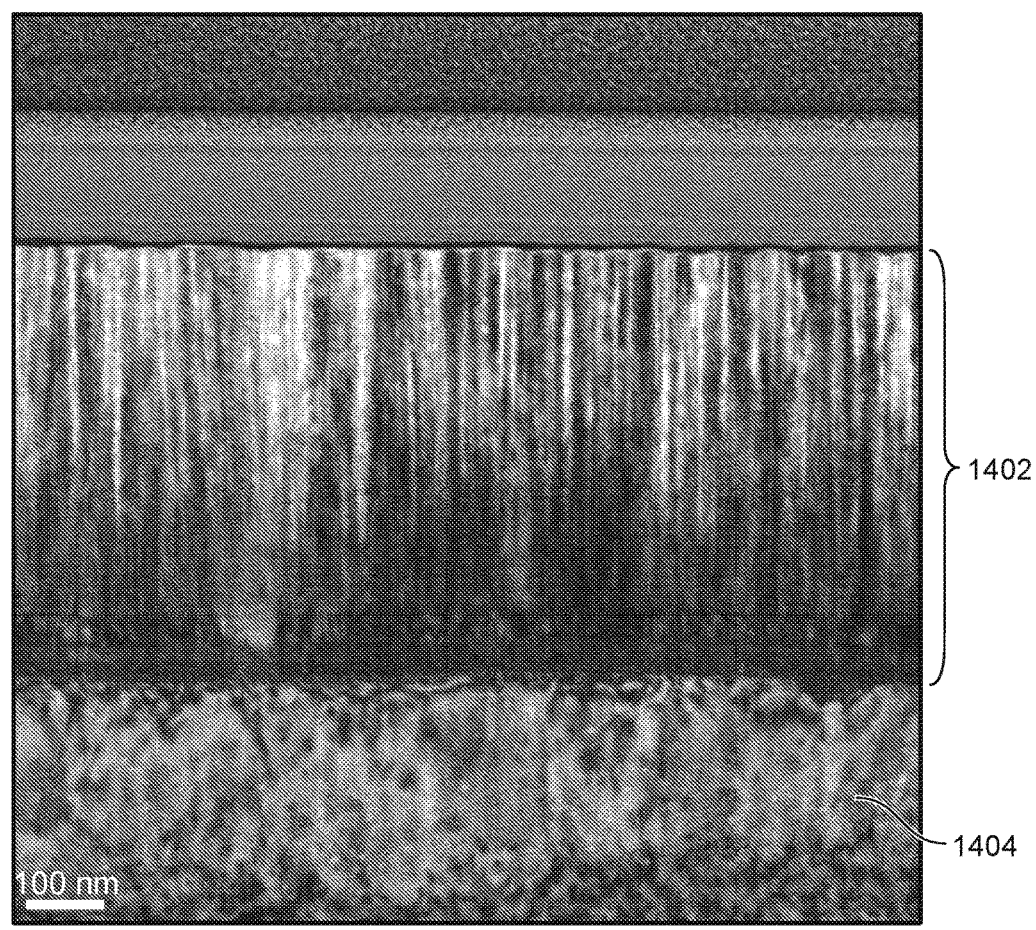
FIG. 14 illustrates a cross-section view of a spongy and porous TiN layer 1402 deposited above a metal layer 1404.
Figure 15:
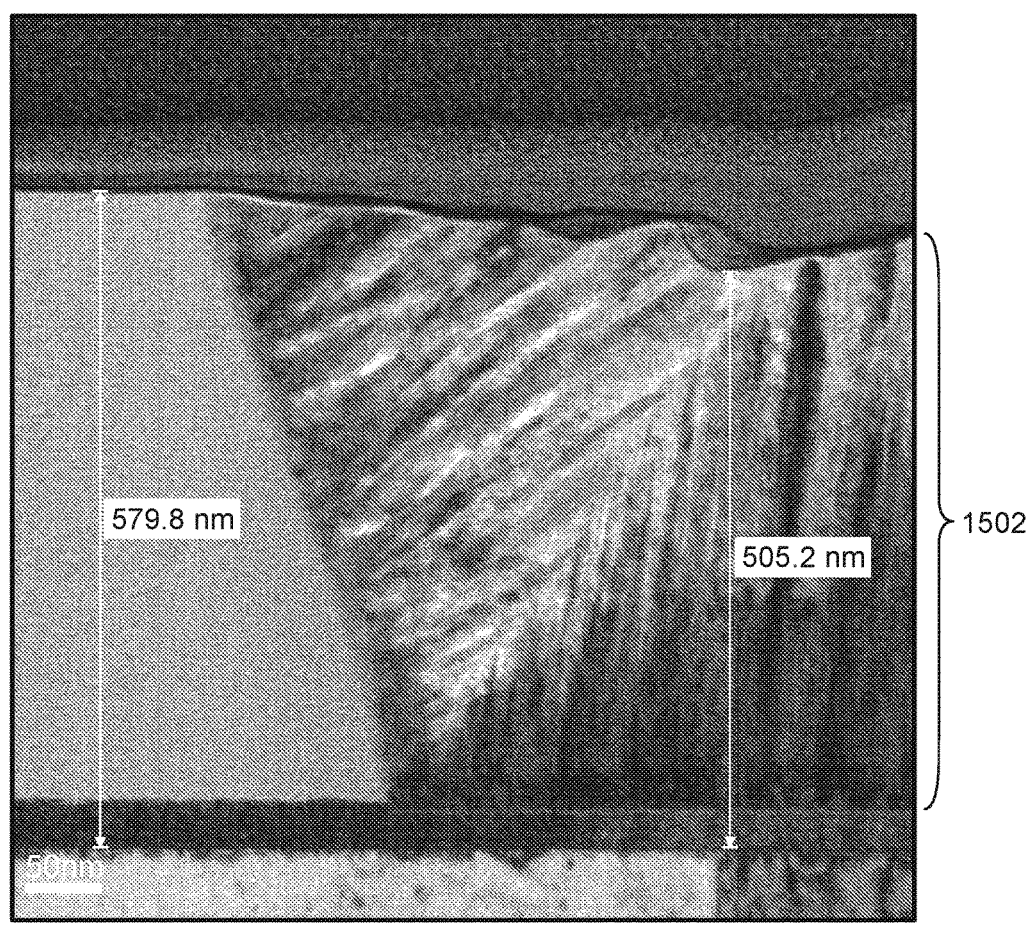
FIG. 15 illustrates another cross-section view of a spongy and porous TiN layer 1502 with TiN columnar structures that are grown from the surfaces of the hole.

FIG. 14 illustrates a cross-section view of a spongy and porous TiN layer 1402 deposited above a metal layer 1404. As shown in FIG. 14, the spongy and porous TiN layer 1402 includes grass-like columnar structures. FIG. 15 illustrates another cross-section view of a spongy and porous TiN layer 1502 with TiN columnar structures that are grown from the surfaces of the hole.

Figure 13D:
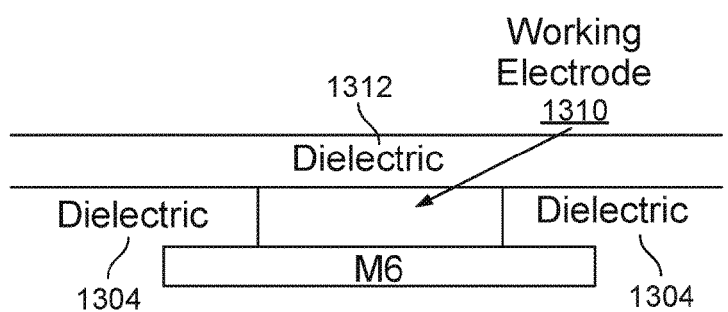

FIG. 13D illustrates step D of the process. At step D, the excess TiN layer is removed. For example, the excess TiN layer may be removed using chemical mechanical polishing (CMP) techniques. The remaining TiN deposited in the hole 1306 forms a spongy and porous TiN working electrode 1310. After working electrode 1310 is formed, a layer of dielectric 1312 (e.g., SiO$_2$) is deposited on top of the dielectric 1304 and working electrode 1310. In some embodiments, the depth of dielectric 1312 is between 100 nm to 5 microns.

Figure 13E:
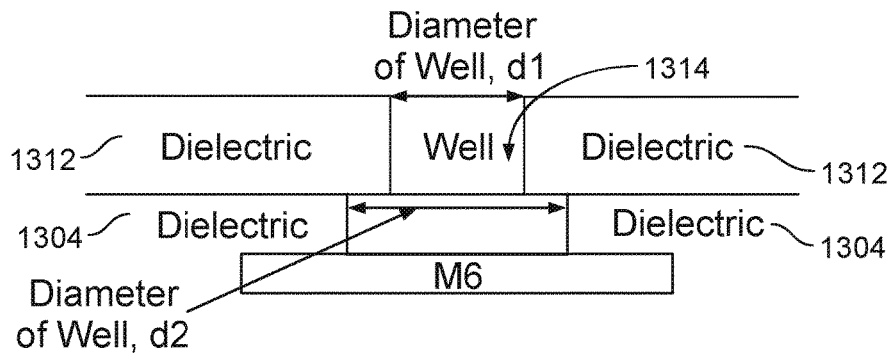

FIG. 13E illustrates step E of the process. At step E, the layer of dielectric 1312 is etched to create a well 1314 exposing only a portion of the upper base surface area of the working electrode. For example, the well may be etched by reactive-ion etching (RIE). Because the base surface area (e.g., $\pi \times (d1/2)^2$) of the opening of the well is independent from the base surface area (e.g., $\pi \times (d2/2)^2$) of the working electrode, $C_{membrane}$ and $C_{electrochemical}$ in the cell may be fine tuned to obtain the desired $C_{membrane}$ and $C_{electrochemical}$ ratio. In some embodiments, the diameter (d2) of well 1314 is between 20 nm to 100 microns.

Building a non-faradaic electrochemical cell 1100 of a nanopore based sequencing chip with a spongy TiN working electrode has many advantages. Depending on the thickness of the TiN electrode (e.g., 500 angstroms to 3 microns thick), the specific surface area of the spongy TiN working electrode and its electrochemical capacitance (e.g., 5 picofarads to 500 picofarads per square micron of base area) have a 10-1000 times improvement over that of a flat TiN working electrode with substantially identical dimensions (e.g., substantially identical thickness and base surface area). Since the spongy TiN working electrode allows electrolyte to diffuse through easily, the diameter/width of the spongy TiN working electrode may extend beyond the diameter/width of the well, such that the base surface area of the well and the working electrode can be optimized independently to provide the desired ratio between $C_{membrane}$ and $C_{electrochemical}$ for improved system performance. Other advantages of using TiN include its low cost and ease of patterning and etching compared to other electrode materials, such as platinum.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:
1. A nanopore cell, comprising:
   a conductive layer;
   a titanium nitride (TiN) working electrode disposed above the conductive layer; and
   insulating walls disposed above the TiN working electrode, wherein the insulating walls and the TiN working electrode form a well into which an electrolyte may be contained, wherein the TiN working electrode forms a base of the well and wherein the insulating walls form surrounding walls of the well, and wherein the surrounding walls extending from the base of the well, wherein a portion of the insulating walls covers a portion of the TiN working electrode, and wherein the well has an opening above an uncovered portion of the TiN working electrode, and wherein a base surface area of the TiN working electrode is greater than a base surface area of the opening above the uncovered portion of the TiN working electrode, and wherein a membrane with a nanopore is formed above the opening of the well.

2. The nanopore cell of claim 1, wherein the TiN working electrode comprises a spongy and porous TiN working electrode that is deposited by a deposition technique with conditions tuned to deposit TiN columnar structures or columns of TiN crystals above the conductive layer.

3. The nanopore cell of claim 2, wherein the spongy and porous TiN working electrode has a specific surface area that is ten to a thousand times that of a specific surface area of a flat TiN working electrode with substantially identical dimensions.

4. The nanopore cell of claim 2, wherein the spongy and porous TiN working electrode has an electrochemical capacitance that is ten to a thousand times that of an electrochemical capacitance of a flat TiN working electrode with substantially identical dimensions.

5. The nanopore cell of claim 2, wherein the spongy and porous TiN working electrode has an electrochemical capacitance between 10 picofarads and 1 nanofarads.

6. The nanopore cell of claim 2, wherein the deposition technique comprises direct current (DC) reactive sputtering from a titanium target, and the conditions tuned to deposit TiN columnar structures or columns of TiN crystals above the conductive layer comprise a temperature, substrate bias voltage, and pressure for sputtering.

7. The nanopore cell of claim 1, wherein the base surface area of the TiN working electrode and the base surface area of the opening above the uncovered portion of the TiN working electrode are selected based on a ratio of a capacitance associated with the TiN working electrode and a capacitance associated with a membrane that spans across the opening.

8. The nanopore cell of claim 2, wherein a portion of the insulating walls covers a portion of the TiN working electrode, and wherein the well has an opening above an uncovered portion of the TiN working electrode, and wherein the electrolyte can diffuse through spaces between the TiN columnar structures or columns of TiN crystals and diffuse vertically down the uncovered portion of the TiN working electrode and then horizontally to the covered portion of the TiN working electrode.

\* \* \* \* \*